(12) United States Patent
Becking et al.

(10) Patent No.: US 9,393,022 B2
(45) Date of Patent: Jul. 19, 2016

(54) TWO-STAGE DEPLOYMENT ANEURYSM EMBOLIZATION DEVICES

(71) Applicant: Covidien LP, Mansfield, MA (US)

(72) Inventors: Frank P. Becking, Santa Clara, CA (US); Karl S. Halden, San Carlos, CA (US); Martin S. Dieck, Campbell, CA (US); Nicholas C. Debeer, Montara, CA (US); Teresa Ruvalcaba, Palo Alto, CA (US); Andre-Jean Lundkvist, Palo Alto, CA (US)

(73) Assignee: Covidien LP, Mansfield, MA (US)

( * ) Notice: Subject to any disclaimer, the term of this patent is extended or adjusted under 35 U.S.C. 154(b) by 246 days.

(21) Appl. No.: 13/962,267

(22) Filed: Aug. 8, 2013

(65) Prior Publication Data

US 2014/0172001 A1     Jun. 19, 2014

Related U.S. Application Data

(63) Continuation of application No. PCT/US2012/024747, filed on Feb. 10, 2012.

(60) Provisional application No. 61/441,845, filed on Feb. 11, 2011.

(51) Int. Cl.
*A61B 17/12* (2006.01)
*A61B 17/00* (2006.01)

(52) U.S. Cl.
CPC ..... *A61B 17/12159* (2013.01); *A61B 17/12113* (2013.01); *A61B 17/12172* (2013.01); *A61B 2017/00526* (2013.01); *A61B 2017/00867* (2013.01); *A61B 2017/12054* (2013.01)

(58) Field of Classification Search
CPC ............... A61B 17/12022; A61B 17/12099; A61B 17/12113; A61B 17/12159; A61B 17/12168; A61B 17/12172; A61B 2017/1205; A61B 2017/12054; A61B 2017/12059; A61B 2017/12063; A61B 2017/12068; A61B 2017/12081; A61B 2017/12086; A61B 2017/1209; A61B 2017/12095
See application file for complete search history.

(56) References Cited

U.S. PATENT DOCUMENTS 3,108,593 A    10/1963   Glassman
4,425,908 A    1/1984    Simon
(Continued)

FOREIGN PATENT DOCUMENTS

CA         2607529        4/2008
CN         101472537 A    7/2009
(Continued)

OTHER PUBLICATIONS

Hill, et al., "Initial Results of the AMPLATZER Vascular Plug in the Treatment of Congenital Heart Disease, Business Briefing," US Cardiology 2004.
(Continued)

*Primary Examiner* — Todd J Scherbel
(74) *Attorney, Agent, or Firm* — Elizabeth A. O'Brien, Esq.

(57) ABSTRACT

Embolic implants, delivery systems and methods of manufacture and delivery are disclosed. The subject implants are deployed in two stages. If sized properly as observed in the first stage, they are deployed to the second stage and detached. If not sized properly in/at the first stage, the implants are designed to be withdrawn and replaced with a more appropriately sized implant or another treatment option selected. Some of the implant configurations may be withdrawn even after the second stage deployment as well.

11 Claims, 6 Drawing Sheets

(56) References Cited

U.S. PATENT DOCUMENTS

| | | |
|---|---|---|
| 4,619,246 A | 10/1986 | Molgaard-Nielsen et al. |
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsante |
| 5,026,377 A | 6/1991 | Burton et al. |
| 5,061,275 A | 10/1991 | Wallsten et al. |
| 5,064,435 A | 11/1991 | Porter |
| 5,104,404 A | 4/1992 | Wolff |
| 5,122,136 A | 6/1992 | Guglielmi et al. |
| 5,158,548 A | 10/1992 | Lau et al. |
| 5,222,971 A | 6/1993 | Willard et al. |
| 5,250,071 A | 10/1993 | Palermo |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,484,444 A | 1/1996 | Braunschweiler et al. |
| 5,499,981 A | 3/1996 | Kordis |
| 5,527,338 A | 6/1996 | Purdy |
| 5,545,208 A | 8/1996 | Wolff et al. |
| 5,545,209 A | 8/1996 | Roberts et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,662,703 A | 9/1997 | Yurek et al. |
| 5,690,671 A | 11/1997 | McGurk et al. |
| 5,702,419 A | 12/1997 | Berry et al. |
| 5,713,907 A | 2/1998 | Hogendijk et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,853,422 A | 12/1998 | Huebsch et al. |
| 5,855,578 A | 1/1999 | Guglielmi et al. |
| 5,879,366 A | 3/1999 | Shaw et al. |
| 5,908,435 A | 6/1999 | Samuels |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,976,162 A | 11/1999 | Doan et al. |
| 5,980,554 A | 11/1999 | Lenker et al. |
| 6,001,092 A | 12/1999 | Mirigian et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,059,813 A | 5/2000 | Vrba et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,106,530 A | 8/2000 | Harada |
| 6,110,191 A | 8/2000 | Dehdashtian et al. |
| 6,123,715 A | 9/2000 | Amplatz |
| 6,139,564 A | 10/2000 | Teoh |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,280,412 B1 | 8/2001 | Pederson, Jr. et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 | 3/2002 | Hieshima et al. |
| 6,368,339 B1 | 4/2002 | Amplatz |
| 6,375,668 B1 | 4/2002 | Gifford et al. |
| 6,379,372 B1 | 4/2002 | Dehdashtian et al. |
| 6,383,174 B1 | 5/2002 | Eder |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 | 9/2002 | Bosma et al. |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 * | 3/2003 | Jacobsen .......... A61B 17/12022 606/157 |
| 6,544,278 B1 | 4/2003 | Vrba et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,302 B2 | 6/2003 | Duerig et al. |
| 6,579,303 B2 | 6/2003 | Amplatz |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,592,605 B2 | 7/2003 | Lenker et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | VanTassel et al. |
| 6,652,556 B1 | 11/2003 | VanTassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,709,465 B2 | 3/2004 | Mitchell et al. |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |

(56) References Cited

U.S. PATENT DOCUMENTS

| | | |
|---|---|---|
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | van der Burg et al. |
| 6,994,717 B2 | 2/2006 | Konya et al. |
| 7,011,671 B2 | 3/2006 | Welch |
| 7,018,401 B1 | 3/2006 | Hyodoh et al. |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,575,590 B2 | 8/2009 | Watson |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 8,454,681 B2 | 6/2013 | Holman et al. |
| 2001/0000797 A1 | 5/2001 | Mazzocchi |
| 2001/0007082 A1 | 7/2001 | Dusbabek et al. |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0111647 A1 | 8/2002 | Khairkhahan et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143239 A1 | 7/2004 | Zhou et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215229 A1 | 10/2004 | Coyle |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1 | 2/2005 | Chanduszko |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0222605 A1* | 10/2005 | Greenhalgh ..... A61B 17/12022 606/200 |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |

(56) References Cited

U.S. PATENT DOCUMENTS

| | | |
|---|---|---|
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0217799 A1 | 9/2006 | Mailander et al. |
| 2006/0229700 A1 | 10/2006 | Acosta et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233224 A1 | 10/2007 | Leynov et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0293935 A1 | 12/2007 | Olsen et al. |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von Oepen et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0262598 A1 | 10/2008 | Elmaleh |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0125094 A1 | 5/2009 | Rust |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0204145 A1 | 8/2009 | Matthews |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2009/0318948 A1* | 12/2009 | Linder ............ A61B 17/12022 606/191 |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030220 A1 | 2/2010 | Truckai et al. |
| 2010/0036390 A1 | 2/2010 | Gumm |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0222802 A1 | 9/2010 | Gillespie, Jr. et al. |
| 2010/0249894 A1 | 9/2010 | Oba et al. |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0054519 A1 | 3/2011 | Neuss |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0226343 A1 | 9/2012 | Vo et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |

(56) References Cited

U.S. PATENT DOCUMENTS

| | | |
|---|---|---|
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0245670 A1 | 9/2013 | Fan |
| 2013/0268053 A1 | 10/2013 | Molaei |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2013/0345739 A1 | 12/2013 | Brady et al. |
| 2014/0005713 A1 | 1/2014 | Bowman |
| 2014/0128905 A1 | 5/2014 | Molaei |

FOREIGN PATENT DOCUMENTS

| | | |
|---|---|---|
| DE | 1283434 B | 11/1968 |
| DE | 102008028308 | 4/2009 |
| DE | 102010050569 A1 | 5/2012 |
| DE | 102011011510 | 8/2012 |
| EP | 743047 A2 | 11/1996 |
| EP | 775470 | 5/1997 |
| EP | 855170 A2 | 7/1998 |
| EP | 1621148 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003-520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 | 1/1996 |
| WO | WO-97/26939 | 7/1997 |
| WO | WO-99/03404 | 1/1999 |
| WO | WO-99/05977 | 2/1999 |
| WO | WO-99/08607 | 2/1999 |
| WO | WO-99/08743 | 2/1999 |
| WO | WO-99/40873 A1 | 8/1999 |
| WO | WO-99/62432 | 12/1999 |
| WO | WO-00/57815 A1 | 10/2000 |
| WO | WO-01/93782 | 12/2001 |
| WO | WO-02/000139 | 1/2002 |
| WO | WO-02/071977 A2 | 9/2002 |
| WO | WO-03/037191 A1 | 5/2003 |
| WO | WO-2005/117718 | 12/2005 |
| WO | WO-2006/026744 | 3/2006 |
| WO | WO-2006/034166 A2 | 3/2006 |
| WO | WO-2006/052322 A2 | 5/2006 |
| WO | WO-2006/091891 A2 | 8/2006 |
| WO | WO-2006/119422 A2 | 11/2006 |
| WO | WO-2007/047851 A2 | 4/2007 |
| WO | WO-2007/076480 A2 | 7/2007 |
| WO | WO-2007/095031 A2 | 8/2007 |
| WO | WO-2007/121405 | 10/2007 |
| WO | WO-2008/022327 A2 | 2/2008 |
| WO | WO-2008/109228 A2 | 9/2008 |
| WO | WO-2008/151204 | 12/2008 |
| WO | WO-2008/157507 A2 | 12/2008 |
| WO | WO-2009/076515 | 6/2009 |
| WO | WO-2009/132045 A2 | 10/2009 |
| WO | WO-2009/134337 | 11/2009 |
| WO | WO-2009/135166 A2 | 11/2009 |
| WO | WO-2010/028314 | 3/2010 |
| WO | WO-2010/030991 | 3/2010 |
| WO | WO-2010/147808 A1 | 12/2010 |
| WO | WO-2011/057002 A2 | 5/2011 |
| WO | WO-2011/057277 A2 | 5/2011 |
| WO | WO-2011/130081 | 10/2011 |
| WO | WO-2011/153304 | 12/2011 |
| WO | WO-2012/068175 A2 | 5/2012 |
| WO | WO-2012/112749 A2 | 8/2012 |
| WO | WO-2012/166804 A1 | 12/2012 |

OTHER PUBLICATIONS

Ronnen, "AMPLATZER Vascular Plug Case Study, Closure of Arteriovenous Fistula Between Deep Femoral Artery and Superficial Femoral Vein," AGA Medical Corporation, May 2007.

Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

U.S. Appl. No. 13/826,298, filed Mar. 14, 2013.

U.S. Appl. No. 13/795,556, filed Mar. 12, 2013.

U.S. Appl. No. 13/669,652, filed Nov. 6, 2012.

* cited by examiner

TWO-STAGE DEPLOYMENT ANEURYSM EMBOLIZATION DEVICES

RELATED APPLICATIONS

This application is a continuation of International Patent Application No. PCT/US20121024747, filed on Feb. 10, 2012, entitled TWO-STAGE DEPLOYMENT ANEURYSM EMBOLIZATON DEVICES, which claims the benefit of and priority to U.S. Provisional Application No. 61/441,845, filed on Feb. 11, 2011, the entire contents of each being incorporated by reference herein.

BACKGROUND

Numerous companies have pursued ball-type embolization devices for aneurysm treatment. Many of these, including the Nfocus LUNA device and other embodiments disclosed in commonly-owned patent applications are designed to be sized to fit a given aneurysm when the implant is fully deployed outside a delivery catheter. The same is true for the braid-ball implants disclosed and produced by Sequent Medical, Inc.

At least with the LUNA device, if size as visualized upon deployment (under active x-ray—i.e., "medical imaging") is acceptable to a physician, the implant is detached. If not, the device is retrieved and exchanged for a more appropriate size. No example of devices designed for intra-aneurysmal treatment are known in which confirmation of final sizing is accomplished under medical imaging where the implant is deployed only up to a pre-selected or identified point. Certainly, embolization coils are often partially deployed within an aneurysm and visualized to determine if their size and/or configuration is acceptable before further advancing the same and effecting release. However, these are not deployed to a specified point as marked on the delivery system for making a size check.

SUMMARY

Generally, braid-balls for aneurysm or other embolization through blood flow disruption and thrombus formation are described. More specifically, variations of the invention concern a subject hub region architecture that may be employed in a single-layer braid ball implant or a double-layer "LUNA" type (i.e., folded-over/flat) implant architecture.

In use, the bulb of the subject implant is deployed in an aneurysm with the estimated final position of the proximal end visualized by aligning a catheter marker with the device proximal end. The implant end may include a band or otherwise (such as by welding) serve as a hub to the braid from which the implant is constructed. Other options as described further below are disclosed as well.

Regardless, if the first stage/bulb "fits", then the adjacent retracted hub region is fully deployed (i.e., the second stage is deployed) and the implant is released from its pusher. The position of the catheter shaft marker and shape of the (first) sizing stage of the implant may be selected from a number of options as shown and described, as well as others.

The shape in the hub region is preferably configured to provide force for self-actuation upon catheter exit. One advantageous configuration is substantially spherical. Another contemplated shape is defined by two conical bodies meeting around a common base. When inset in a more curvilinear (heart-shaped) in cross section, the deployed hub can provide additional blood flow satiation zone(s) within the implant.

In any case, the inset is provided such that it can retract even when the implant is compressed to fit a high aspect ratio aneurysm. As demonstrated, the implant is operable in a pocket simulating an aneurysm with a dome-to-width ratio of about 2:1. Based on the implant configuration, higher ratios will be possible as well.

The exemplary embodiment demonstrating such activity employs a small spherical inset region. The inset region was defined over a spherical ball about 3 mm in diameter, for an implant between at least about 6-7 mm in gross outside diameter. Thus, the nested inset region can fully expand even within the outer bulb when partially compressed. When using the double-cone shape for the inset region, the additional stored energy available at the medial crease can be of further assistance driving inset shape recovery. Moreover, the conical taper can provide improved clearance for full expansion of the inset form in cases where the outer body or bulb of the implant is further compressed.

The distal/terminal end of the implant and any associated proximal hub/band may be positioned at the periphery of the bulb of the implant when fully deployed, or more inset in varying degrees. When employed in a "LUNA" folded-flat configuration, the distal marker of the implant is internal and a tether extends to the proximal hub of the device. In a one-layer implementation (i.e., a configuration that presents one layer at the distal end of the implant with the option of more at a proximal side depending on inset shape configuration) the distal marker be provided by a radiopaque material (e.g., Pt) band capturing the braid. As to the proximal side of either such device, it may comprise a radiopaque band capturing the braid. As discussed in US Patent Application No. 2011/0319926 (Becking, et al.) another option is to remove the band after the braid has been glued to create a composite hub construct.

In yet another variation, no such hub or band is provided at the proximal end of the braid defining the implant. Instead, a length of braid (between about 1 and about 2 mm long) is employed as a delivery system interface. Such a "tail" or sleeve of braid, when confined within a catheter is able to firmly grip/interlock with a complementary delivery system surface. In such a system, the delivery system surface is also advantageously covered or constructed of braid of a similar wire size and configuration to promote interlocking. Once the implant is free of the catheter, the (formerly) confined sleeve of braid defining the implant tail opens to permit the inner delivery system pusher member to be pulled free.

The forming method for a LUNA-style hidden hub implant is detailed herein in two heatsetting stages. Stage 1 produces a double-layer "folded-flat" implant preform with a columnar inset. Stage 2 changes the shape of the inset into a spherical volume. In the second forming and heatsetting procedure, a proximal suture tie may be employed in defining a second folded-flat region like that at the distal side as formed in Stage 1. The second heatsetting cycle may also be employed to modify the shape of the outer bulb. For example, while retaining the "folded-flat" distal bend(s), the gross shape of the bulb may be compressed from a substantially cylindrical shape to a more squat or flattened "M&M" shape (e.g., ellipsoidal). So-shaped, greater radial force is available for aneurysm fit and/or a greater range of treatment sites made available. Further reference to heatsetting methodology and delivery systems as may be applied to the present invention are presented in U.S. patent application Ser. No. 12/465,475 and PCT/US2009/041313 and U.S. patent application Ser. No. 12/942,209 and PCT/US2010/56051, each incorporated by reference in its entirety.

Other manufacture techniques are applicable as well. For instance, a selective heat treatment approach is contemplated in which a portion of the implant performing being shaped is set over a ferromagnetic material (e.g., 304 magnetic stainless steel alloy) and is heated through induction utilizing a radio-frequency (RF) field. Such an approach strictly localizes the heat treatment to areas in contact with the induction-heated element. To insure that no other material is significantly heat-affected, such activity may be conducted under the flow of coolant such as Nitrogen or Argon gas or some other medium. In any case, such an approach may be advantageously used in the "Stage 2" operation described above for re-shaping the inset region, without applying a second heat treat to the remainder of the implant preform.

The body of the subject implants may be constructed of NiTi alloy that is superelastic at human body temperature. Advantageously, the wire is in the size range of 0.0008 to 0.0013 inches, although it may be larger or smaller. It may be etched pre- and/or post-heat treatment using AYA solution or by such processes employed by service providers including NDC, Inc. Binary Nitinol alloy may be employed, or the alloy may include Au, Pt, W, Ir, Pd, alloys thereof or another dense element to improve radiopacity. Another approach to improving radiopacity contemplates using a plurality of such wires or ribbons intermixed when braiding with Nitinol. Otherwise, Pt core Nitinol Drawn Filled Tube (DFT) may be employed or other means.

The braid matrix is particularly effective in promoting thrombosis in order to embolize an aneurysm as its density increases. For a given catheter crossing profile, a certain maximum braid configuration is possible. For example, "folded-flat" implants as further described herein that are intended to track to the neurovasculature through commercially available 3 Fr/0.027 inch catheters (such as the REBAR or MARKSMAN) may be constructed from a 72×0.001" braid configuration (as originally provided or etched thereto) or 96×0.0009" braid (ditto) configuration. In single layer implant architectures, 144-end braid configurations are feasible with similar crossing profile with wire size in the range of about 0.008 to about 0.0011 inches in diameter. Still, it is to be noted that higher end count braid (e.g., 192 or 288) can be employed in the subject invention as can other braid end multiples/configurations. Likewise, it is possible to construct braided implants indented for 0.021 inch catheter compatibility. These may advantageously use two layers of 48×0.001" braid or higher "end" multiple counts in thinner wire/filament or single-layer 72 or 96 end braid selections, etc.

In any case, the subject inventions include the devices, kits in which they are included, methods of use and methods of manufacture. More detailed discussion is presented in connection with the figures below.

BRIEF DESCRIPTION OF THE FIGURES

The figures provided herein are not necessarily drawn to scale, with some components and features exaggerated for clarity. Variations of the invention from the embodiments pictured are contemplated. Accordingly, depiction of aspects and elements of the invention in the figures are not intended to limit the scope of the invention.

DETAILED DESCRIPTION

Various exemplary embodiments of the inventive aspects are described below. Reference is made to these examples in a non-limiting sense. They are provided to illustrate more broadly applicable aspects of the subject inventions. Various changes may be made to the subject matter described and equivalents may be substituted without departing from the true spirit and scope of the invention(s).

Aneurysm Embolization Systems

The embodiments described herein are specifically designed so that, when deployed to a given stage within an aneurysm, the size of this stage is representative of the final size and configuration of the implant upon final deployment with the delivery system. Several advantages can be achieved in conjunction with such a system. One such advantage involves the opportunity to minimize delivery profile and/or complexity given the unique implant/delivery system interaction enabled. Another advantage involves the opportunity to provide larger implant sizes for a given delivery profile. Still another set of advantages involves the ease of expanded implant recapture, together with associated procedural and patient safety advantages. All told, aspects of the present invention (alone and/or in combination with one another) provide for a new and useful system for neurovascular aneurysm treatment or for treating other vascular, pocket-type or luminal defects.

Figure 1:
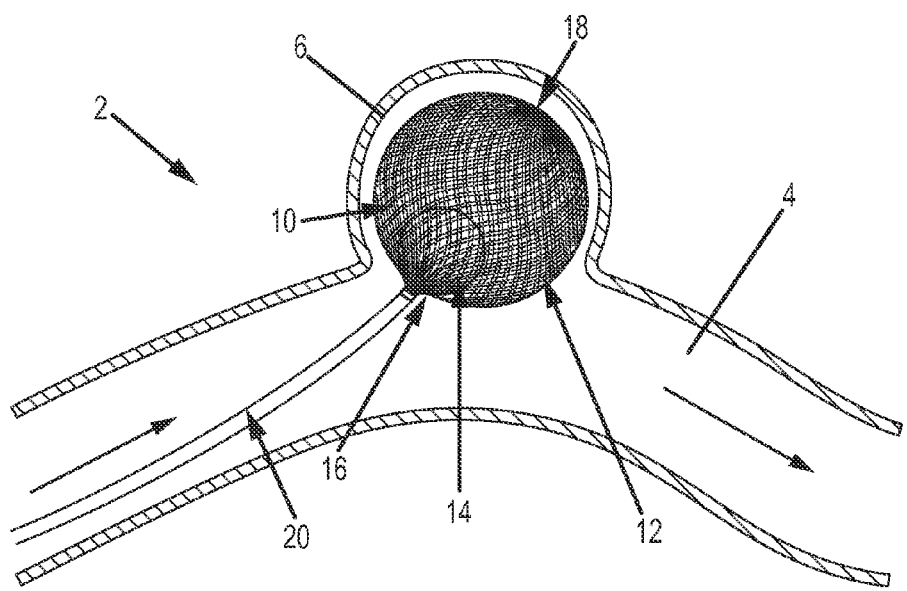
FIG. 1 illustrates a variation of the subject implant deployed in an side-wall aneurysm model.

FIG. 1 shows an implant 10 delivered according to the subject methodology as deployed in an side-wall aneurysm model 2. The model includes a parent vessel 4 and aneurysm fundus 6 filled by the implant 10. The implant is delivered in association (preferably via a detachable association vs. simple abutment) with a pusher 20. The implant comprise an outer bulb 12 and a substantially spherical inset region 14. A dense and complex structure is thus presented to the direction of blood flow (as indicated by arrows) to help promote blood thrombosis via disruption of its flow. Markers are optionally present at proximal and distal extents 16, 18 of the implant.

Figures 2A, 2B, 3A, 3B:
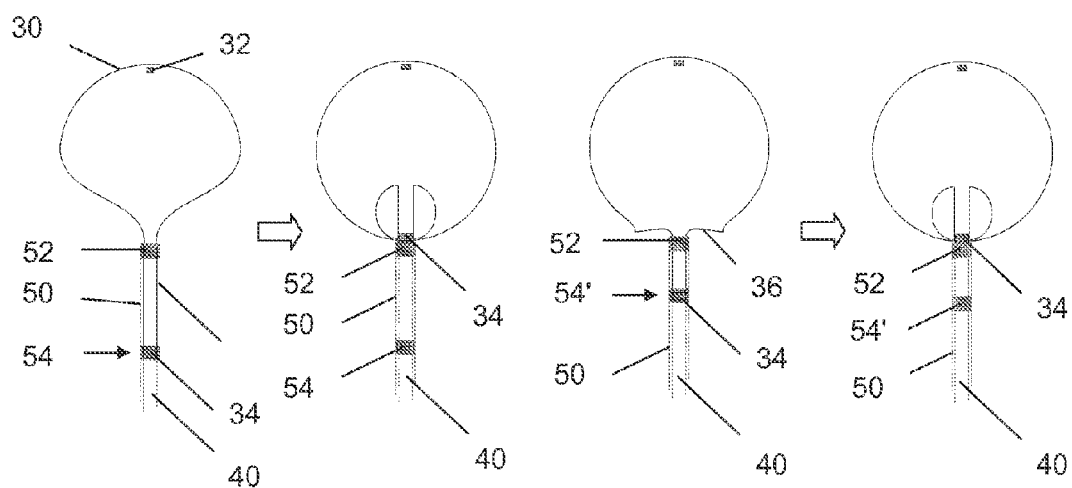
FIGS. 2A and 2B and FIGS. 3A and 3B diagrammatically illustrate an implant in use with coordinated catheter systems at different first and second stages of implant deployment, respectively.

FIGS. 2A and 2B and FIGS. 3A and 3B diagrammatically illustrate the implant in use with coordinated catheter systems. FIGS. 2A and 2B illustrate one optional approach to staged deployment; FIGS. 3A and 3B illustrate another. All of these figures illustrate a generic distal implant architecture 30 in which a distal marker 32 diagrammatically pictured. In each view, the implant includes a proximal hub/marker band 34 operating as an interface region to an (optionally detachable) pusher 40. The hub and pusher may be connected by a mechanical detachment interface as described in the above-referenced patent applications, an electrolytically-severable joint, a meltable polymer filament, etc. In any case, the pusher is shown within the end of a microcatheter 50. The microcatheter includes a distal marker 52 and a more proximal reference marker 54.

In FIG. 2A, the reference marker is set at a position such that when the implant proximal hub/marker 34 is aligned therewith the freed/expanded portion of the implant is deployed in a "teardrop" of approximately the same height of the finally deployed implant shape as shown in FIGS. 2B and 3B. Likewise, the catheter reference marker shown 54' in FIG. 3A is positioned such that a "mushroom" shape with flats 36 is produced upon hub 34 alignment therewith. Again, this intermediate implant body shape is similarly sized to the finally delivered implant configuration.

As such, at either intermediate stage of delivery (i.e., in a system configured per FIG. 2A, 3A or related thereto) a physician can determine if the implant is the proper size selected for the aneurysm to be treated by visualizing the position of the distal marker 32 in/on the implant and the distal marker 52 of the catheter. If the distal marker of the catheter is positioned at the neck of the aneurysm when the implant is in the first/intermediate stage of delivery, then the physician is offered an indication (mid-procedure) that upon completion of implant deployment that the proximal surface of the implant will be likewise so-positioned, as desired. Thus, an aspect of the invention concerns a catheter with a marker system and an implant (or an implant pusher as further described below) that include radiopaque markers coordinated for a first "check" stage of deployment followed by a "final" release/released deployment stage.

Figure 4A:
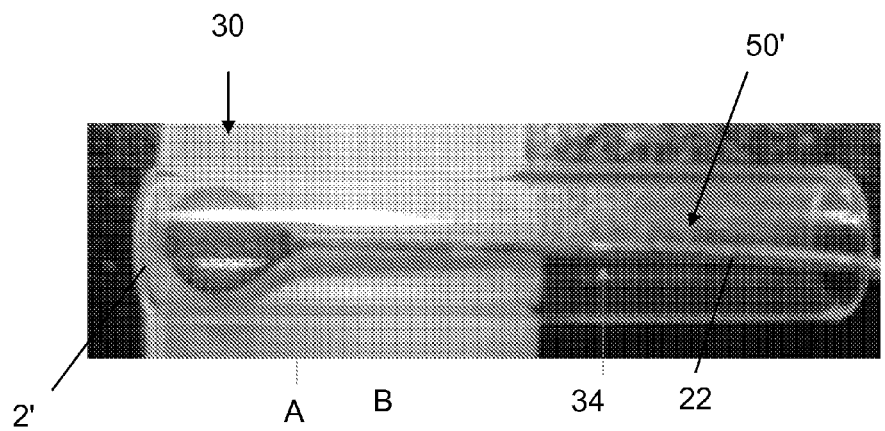
FIGS. 4A-4D illustrate the implant construction from FIG. 1 visualized through a clear catheter in the stages of deployment represented in FIGS. 2A-3B.
Figure 4B:
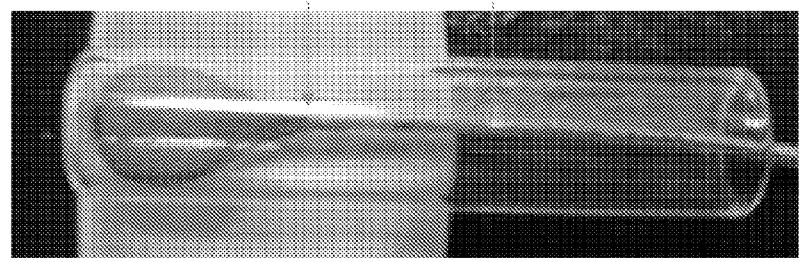
Figure 4C:
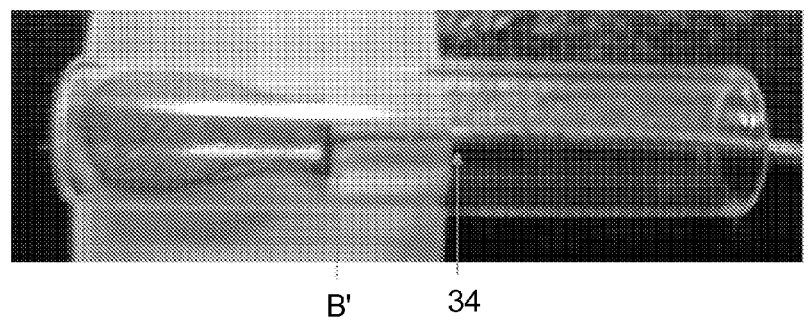
Figure 4D:
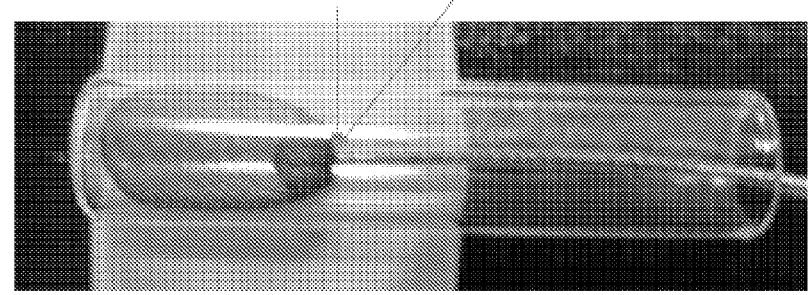

FIGS. 4A-4D illustrate the implant construction in stages of deployment visualized within a glass vial serving a second model 2'. The implant 30 is shown at various positions confined within a clear sheath 50' simulating a catheter. Proximal to a marker element 34 seen in each image is a coil-reinforced length 22 simulating a pusher. FIG. 4A illustrates the implant in a first stage of the deployment of bulbous portion with the catheter end at point A. In FIG. 4B, the full-size teardrop sizing-check shape has developed with the catheter end at point B. With little or no substantial change in height, the mushroom sizing shape is developed with the catheter end at point B'. As evident from movement of marker 34, however, the pusher has been advanced. Upon advancement of the pusher and marker 34 to its ultimate/final position before pusher detachment, the final implant shape is formed with no significant difference in the position of the proximal face of the implant as evident by the alignment of the lead-line arrows.

Figure 5A:
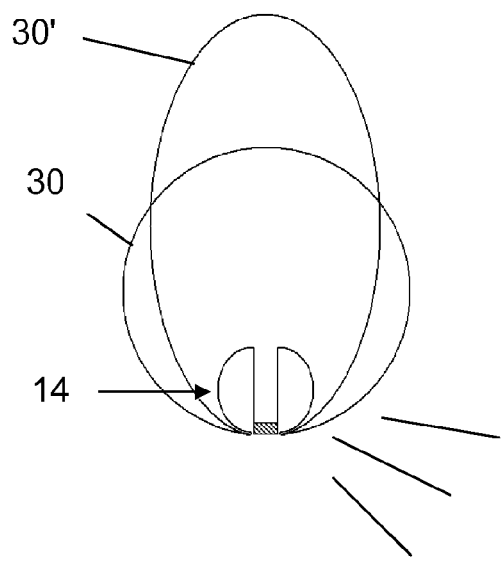
FIGS. 5A-5F illustrate inset configuration variations.

Notably, all of the figures up to this point illustrate an inset region 14 configuration as shown in cross section per FIG. 5A. Likewise, FIG. 5A illustrates the manner in which the sizing of the inset region 14 accommodates different compression factors 30, 30' of the same implant ball or bulb. The relatively small(er) spherical inset configuration in FIG. 5A is advantageously formed as further described below. Moreover, it demonstrates robust recovery and actuation as pictured. However, other inset shapes or forms offer further advantages and options as described below.

Figure 5B:
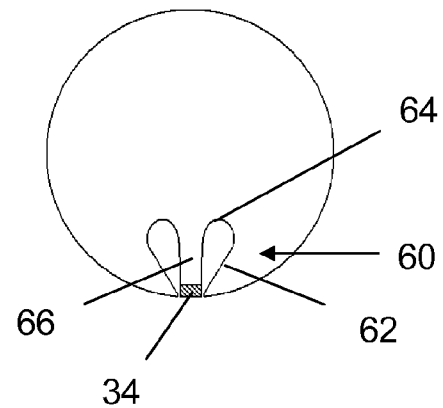
Figure 5C:
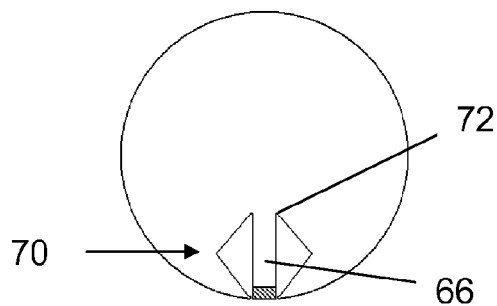

For example, FIG. 5B illustrates an inset 60 that is "heart shaped" in cross section. Such an inset offers additional clearance for bulb compression along a conical proximal section 62. Yet, the curve 64 to the distal section facilitates recapture of the device even after complete exit of extension 66 and hub 34 from the delivery catheter. By way of contrast, a double-conical shaped inset 70 as shown in FIG. 5C may "lock" with the catheter at the deeply inset "V" junction 72. Yet, the double-cone shape may be desirable because the increased number of sharp bends or transitions within the profile can help drive predictable shape recovery and increase resistance to radial compression within the proximal portion of the device.

Figure 5D:
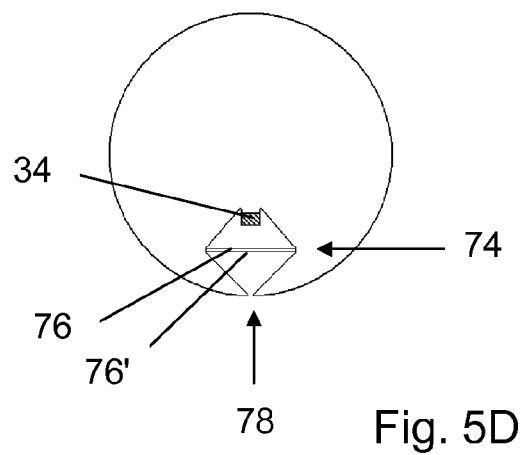

FIG. 5D illustrates a second species of conical inset 74. In this variation, the two cones are adjacent, each with its own base 76, 76' instead one that is conjoined. Further, FIG. 5D illustrates the manner in which any "tail" or extension section of the braid connecting to the hub 34 can be made short or essentially eliminated as compared to the previous variations. Moreover, the upper and lower cones are set at different angles so as to close the proximal end of the device at 78. Naturally, the previous inset variations can receive similar treatment as well.

Figure 5E:
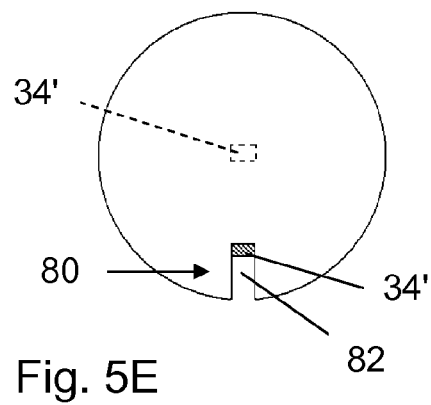
Figure 5F:
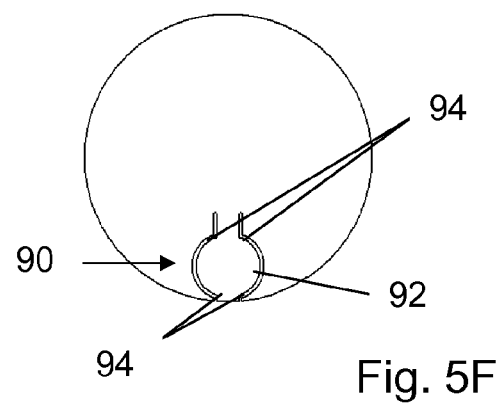

FIG. 5E illustrates an approach in which the entry/exit port of the hub 34' is inverted. Thus, recapture into a catheter requires a 180 degree bend form at the braid/hub junction. It will track the same way in the catheter for deployment. Such a feature may limit catheter downsizing. However, this feature can be accommodated by utilizing finer wire (e.g., 0.0008 inch diameter or less) able to bend in a tighter radius than heavier wire.

Again, the length or position of the inset extension 82 can be varied. For example, it may be desirable to extend it such that the position of the hub marker 34' appears in roughly the center of implant 30 when uncompressed as illustrated in dashed line. Such an approach may be desirable when intending to fill a cavity with multiple numbers (e.g., in a multi-ball treatment approach to giant aneurysm) of the same implant that are allowed to fully expand, rather than form-fitting a single implant to fill an aneurysm. In which case, the hub can serve as a single, centrally-located marker.

Figure 6A:
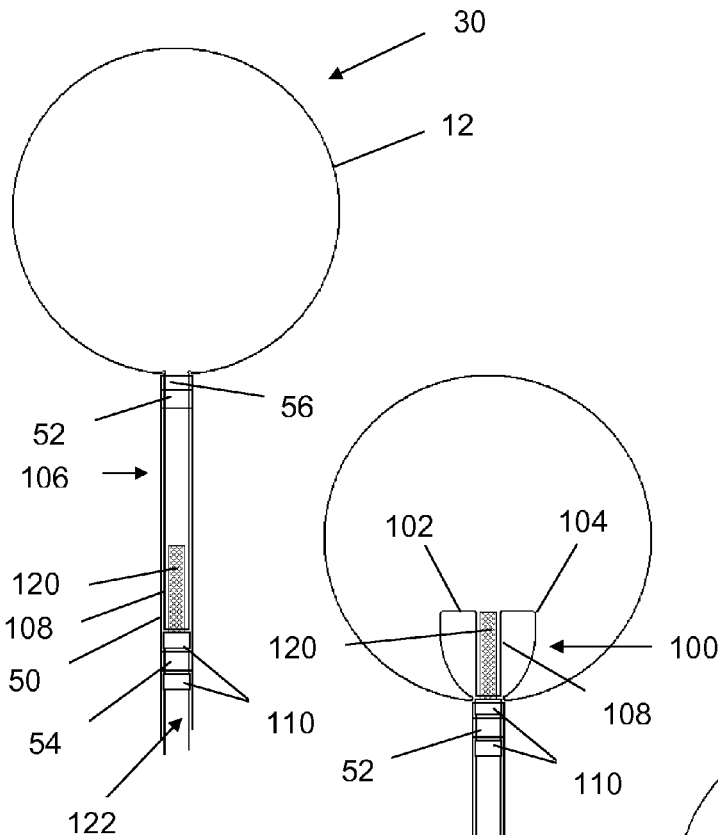
FIGS. 6A-6C illustrate deployment of an implant with a hubless delivery system interface employing yet another inset configuration.
Figure 6B:
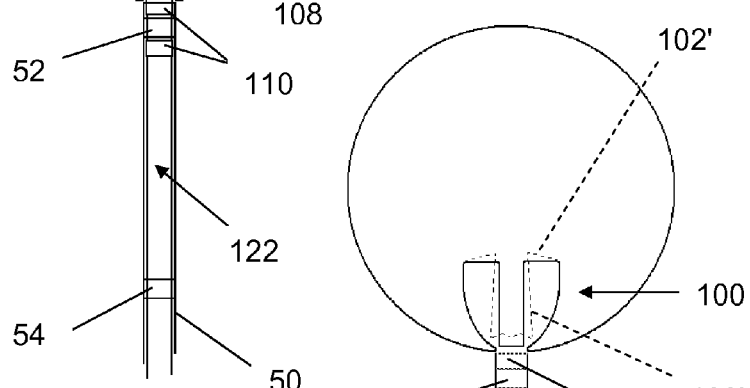
Figure 6C:
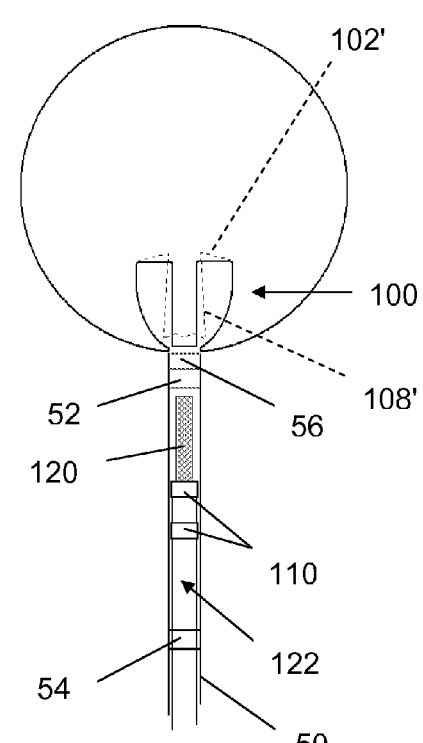

Next, FIG. 5E illustrates an inset 90 that includes no hub and/or marker arrangement. Instead, this inset is configured especially for use with a delivery system as illustrated in FIGS. 6A-6C. Its shape is set to open when uncompressed by a catheter at bulb 92, while offering additional compression force at bends 94 for delivery system securement (via increased linear pressure) when the shape is compressed within the delivery catheter.

With respect to FIGS. 6A-6C, these illustrate an implant 30 with a urn or vase-shaped inset 100 as shown deployed/developed in FIGS. 6B and 6C. Such an inset offers advantageous proximal-side clearance, with a flat top 102 reducing inset height, and a distal crease 104 storing energy upon compression to drive shape recovery upon catheter release.

More generally, FIG. 6A illustrates implant 30 with bulb 12 outside of a delivery catheter 50 and implant tail 106 (before it transforms into the inset shape 100) still located therein. An interface segment 108 of the tail surrounds a textured (optionally by matching braid) retention section 120 of a pusher 122.

The whole length of the pusher may comprise metal braid which is encased/co-extruded by Polyimide with the distal section ablated from the braid. Components for such construction and ablation services are available from Microlumen, Inc. Tapered flex can be designed into the shaft by further selective ablation and/or including a taper-ground wire (floating or bonded) within a lumen of the pusher construction.

The delivery microcatheter includes a distal soft tip 56 and distal marker 52. A proximal reference marker 54 on the catheter is shown located between a pair of reference markers 110 on pusher 122. So long as the catheter holds the implant interface section compressed to the pusher retention section, the implant can be retrieved.

However, upon full deployment as shown in FIG. 6B, the interlocking interface between the implant and pusher is lost. At this point, pusher 122 may be withdrawn as shown in FIG. 6C and the catheter withdrawn as well. As positioned, the distal end of the catheter continues to mark the proximal position of the implant as the pusher is withdrawn, with only a small gap.

Also noteworthy is manner in which the inset may be shaped to facilitate implant release. As illustrated by dashed line of features 102' and 108' in FIG. 6C, the inset may be shaped to specifically pull-away from the pusher retention section upon exit from the delivery microcatheter.

Implant Manufacture

As referenced above, the subject implant architecture may be employed in a single layer braid ball implant or a double-layer LUNA type (folded-over/flat) approach. FIGS. 7A-7D illustrate aspects of manufacture in the latter case. Further details may be appreciated in reference to the application Ser. Nos. 12/465,475 and 12/942,209 and PCT/US2009/041313 and PCT/US2010/56051, each of which is incorporated by reference in its entirety.

Figure 7A:
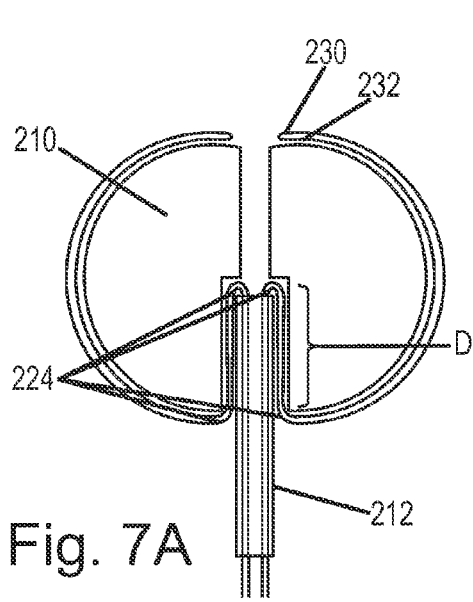
FIGS. 7A-7D illustrate stages of implant production.

As illustrated in FIG. 7A, a "Stage 1" or "Intermediate" state implant preform 200 can be shaped and heatset in association with internal heatsetting tooling element or form 210 and such other elements as described in the referenced descriptions with the addition of a deep columnar inset 202 formed with sleeve 212. With a close-fit relation between the layers of braid 230, 232 and the form elements 210, 212 tight radius bends are set at the turns 224 as indicated.

Figure 7B:
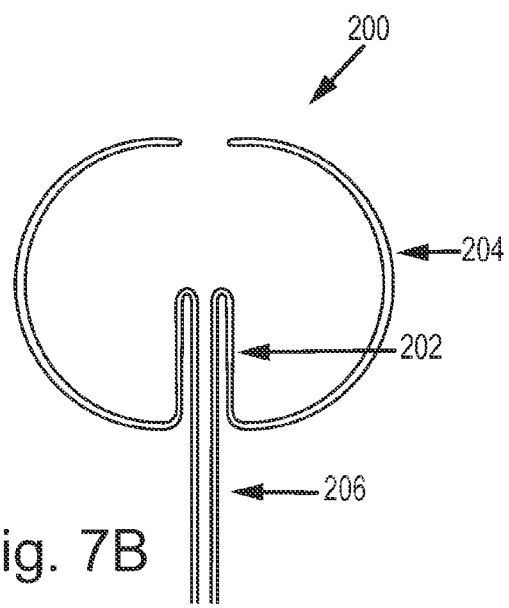
Figure 7C:
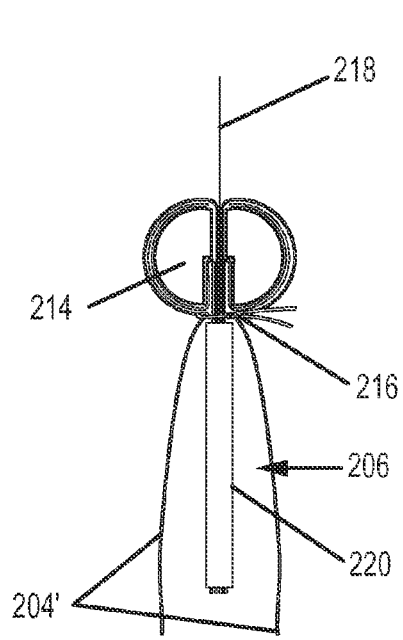
Figure 7D:
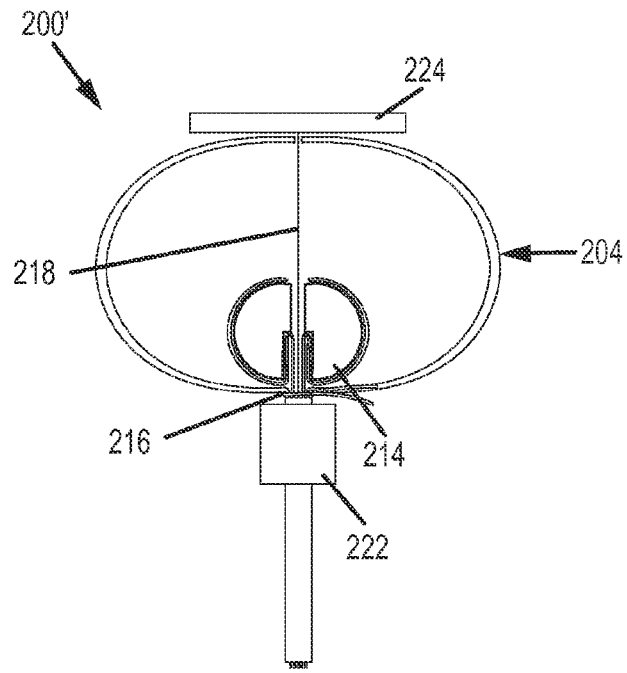

Once freed of the form elements as shown in FIG. 7B, preform 202 is better visualized as including a generally bulbous portion 204 along with inset 202 and extension or tail region 206. The depth "ID" of the inset is coordinated to facilitate its acceptance of a secondary internal form 214 as shown in FIG. 7C. With a tie 216 to hold it in place, the extent of the bulb 204 (shown as inverted sections 204' FIG. 7C) can be reversed or "flipped" back into shape as shown in FIG. 7D.

With a mandrel 218 secured (e.g., by a metal tie 220) in position relative to form 214, a shoulder 222 can be used to compress a proximal fold 234 in the device, and a table or flat 222 can be used to compress the bulb against table element 224 into a modified shape (in this case more "squat" or ellipsoidal in cross-section) in a second heatsetting step to define a "Stage 2" of "Final" shape preform 200'.

Figure 8:
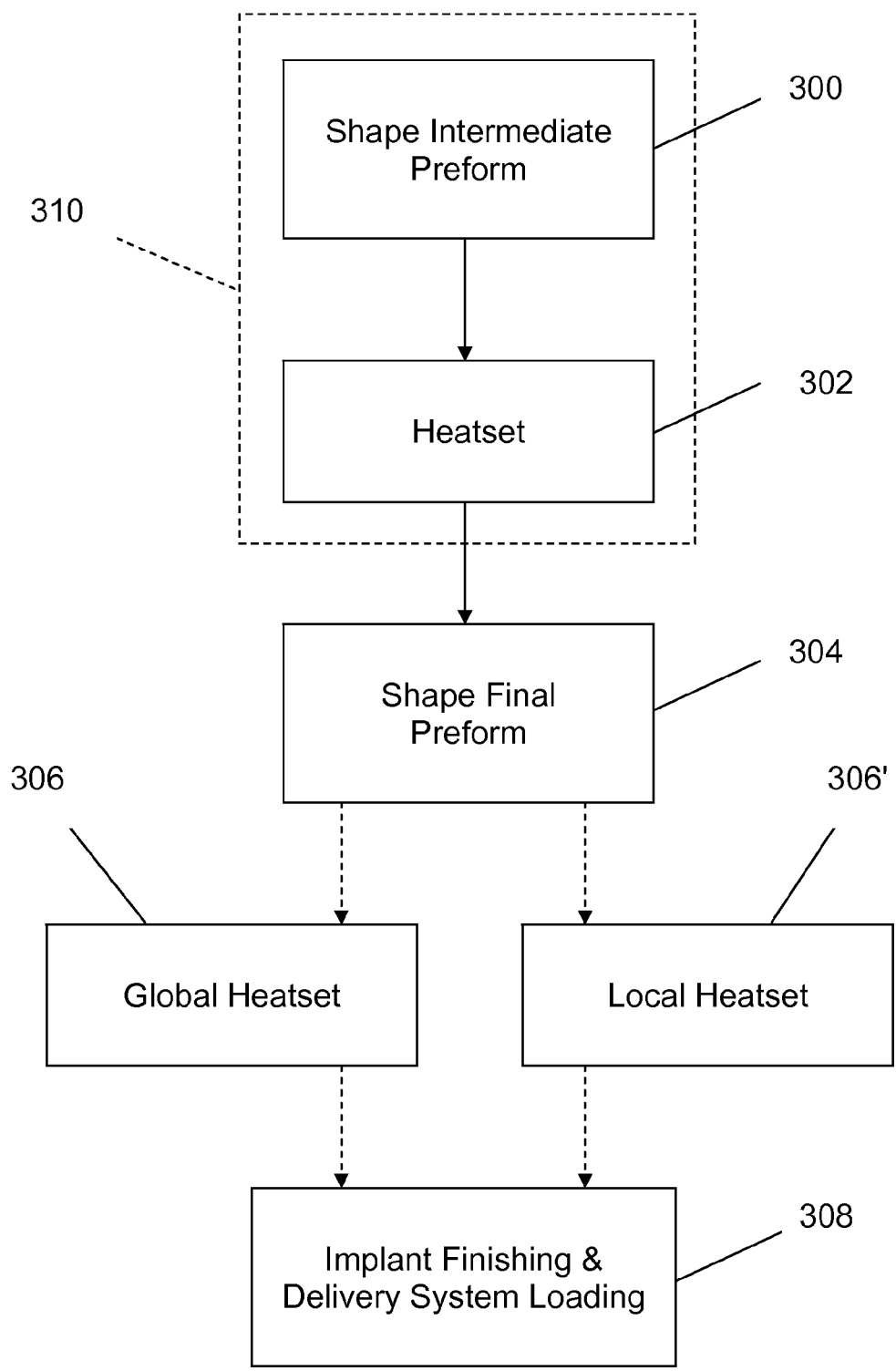
FIG. 8 is a flowchart showing various implant manufacture options.

Such a process flow path is illustrated as the left path in the flowchart of FIG. 8. Specifically, after forming the native braid (previously heatset or not) from which the implant is constructed over and within mandrel/form pieces at 300, the body is heatset at 302. Freed from the first set of heatsetting fixtures, it is optionally reshaped/reformed at 304, followed by a second overall heatsetting procedure 306. Finally, at 308, further processing such as optionally hubbing with marker bands, installing other marker features, hub welding, etc. is performed and then loading onto any optional delivery system pusher, onto packaging and sterilization as is common.

As an alternate flow path, after the first heatsetting and second shaping, only the inset is heatset at 306'. This can be accomplished as described above using a ferromagnetic material and induction field to concentrate heat for setting the shape of the braid in contact with element 214, for example.

Generally when the braid comprises Nitinol, any such heatsetting is accomplished between 500-550° C. for a period up to about 5 minutes. Such heating may be followed by quenching in water or be otherwise performed.

Regardless, it is further contemplated that the entire shaping of the implant may occur in one more complex cycle 310 in which each of the bulb and inset portions of the implant are formed simultaneously over a more complex set of nested forms. Such an approach may be especially viable when the implant only comprises a single layer of braid instead of also including a folded-flat distal section.

Variations

The subject methods may include each of the physician activities associated with implant positioning and release. As such, methodology implicit to the positioning and deployment of an implant device forms part of the invention. Such methodology may include placing an implant within a brain aneurysm, or at parent vessel targeted for occlusion, or other applications. In some methods, the various acts of implant introduction to an aneurysm or parent vessel are considered. More particularly, a number of methods according to the present invention involve the manner in which the delivery system operates in reaching a treatment site, for example. Other methods concern the manner in which the system is prepared for delivering an implant.

Also, it is contemplated that any optional feature of the inventive variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural references unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. All references cited are incorporated by reference in their entirety. Although the foregoing invention has been described in detail for purposes of clarity of understanding, it is contemplated that certain modifications may be practiced within the scope of the appended claims.

The invention claimed is:

1. An aneurysm treatment system comprising:
a catheter with a distal marker and a proximal reference marker;
an implant pusher; and
an implant connected to a distal end of the implant pusher and comprising a bulbous portion and a tail portion, the tail portion adapted to be received in a linear configuration within the catheter with a distal end of the tail portion being proximal to the bulbous portion when the implant is in an intermediate stage, the tail portion defining an inset within the bulbous portion when the implant is in a final stage,
wherein at least one of the pusher and the implant comprises an implant marker, wherein when the implant marker is aligned with the proximal reference marker, the implant is in the intermediate stage with the bulbous portion of the implant deployed from the catheter, wherein, when the implant marker is aligned with the distal marker, the implant is in the final stage with the implant deployed from the catheter and the tail portion defining the inset within the bulbous portion, wherein the implant has a height that is approximately the same in the intermediate stage and in the final stage.

2. The system of claim 1, wherein the bulbous portion has a teardrop shape in the intermediate stage.

3. The system of claim 1, wherein the bulbous portion has a mushroom shape in the intermediate stage.

4. The system of claim 1, wherein the inset is configured to be recapturable in clinical use.

5. The system of claim 1, wherein the inset is configured so that it is not recapturable in clinical use.

6. The system of claim 5, wherein the inset is substantially spherical.

7. The system of claim 5, wherein the inset has an opposing cone shape.

8. The system of claim 5, wherein the inset includes an inverted hub.

9. The system of claim 5, wherein the inset includes no hub.

10. The system of claim 9, wherein the inset is adapted to expand from a compressed conical shape.

11. The system of claim 10, wherein the inset is adapted to expand into the bulbous portion.

* * * * *